United States Patent [19]

Kurath et al.

[11] 4,183,920
[45] Jan. 15, 1980

[54] 4-N-ACYL, 2'-N-ACYL AND 4,2'-N,N'-DIACYLFORTIMICIN E DERIVATIVES

[75] Inventors: Paul Kurath; John S. Tadanier; Jerry R. Martin, all of Waukegan, Ill.

[73] Assignee: Abbott Laboratories, North Chicago, Ill.

[21] Appl. No.: 863,010

[22] Filed: Dec. 21, 1977

[51] Int. Cl.$^2$ .................. A61K 31/71; C07H 15/22
[52] U.S. Cl. .................. 424/180; 536/17 R; 536/4
[58] Field of Search .................. 536/17; 424/180

[56] References Cited
U.S. PATENT DOCUMENTS

| | | | |
|---|---|---|---|
| 3,931,400 | 1/1976 | Nara et al. | 424/118 |
| 3,976,768 | 8/1976 | Nara et al. | 424/118 |
| 3,985,727 | 10/1976 | Daniels | 536/17 |

Primary Examiner—Johnnie R. Brown
Attorney, Agent, or Firm—Robert L. Niblack; Gildo E. Fato; Joyce R. Niblack

[57] ABSTRACT

4-N-Acyl, 2'-N-acyl and 4,2'-N,N'-diacylfortimicin E derivatives represented by the formula

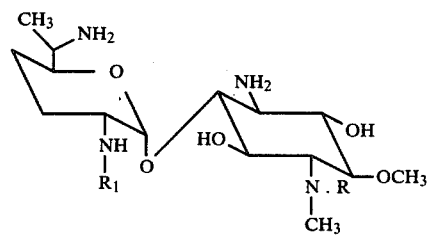

wherein R is hydrogen, acyl, aminoacyl, N-lower alkylamino acyl, N,N-diloweralkylaminoacyl, hydroxy-substituted aminoacyl or an amino acid residue; $R_1$ is hydrogen, acyl, aminoacyl, N-loweralkylaminoacyl, N,N-diloweralkylaminoacyl, hydroxy-substituted aminoacyl or an amino acid residue, with the limitation that R cannot be hydrogen when $R_1$ is hydrogen, and $R_1$ cannot be hydrogen when R is hydrogen; the pharmaceutically acceptable salts thereof; intermediates therefor; pharmaceutical compositions; and methods of making and using the compounds. The compounds are useful as antibiotics.

18 Claims, No Drawings

4-N-ACYL, 2'-N-ACYL AND 4,2'-N,N'-DIACYLFORTIMICIN E DERIVATIVES

BACKGROUND OF THE INVENTION

Despite the availability of a variety of highly effective antibiotics, the search for new antibiotics is a continuing one. The primary reason for the continuing search is the reoccuring development of microorganisms which are resistant to existing antibiotic therapy. Thus there is a continuing need for new antibiotics which are either intrinsically more active than existing drug entities and thus can be administered in lower dosages to minimize the side effects of these powerful drugs, or are effective against resistant strains.

A number of aminoglycoside antibiotics are known, such as the gentamicin and kanamycin family of antibiotics. More recently, a new family of aminoglycosides, the fortimicins have been identified. See, for example, U.S. Pat. Nos. 3,976,768 and 3,931,400 which disclose Fortimicin A and B.

Although the fortimicin family is a relatively new group of antibiotics, clinical experience has shown that aminoglycoside antibiotics are susceptible to the resistant strain problem. In many cases, the resistance is R-factor mediated and is attributed to the ability of the bacteria to enzymatically modify the amino or hydroxy groups of the aminoglycoside antibiotics. Thus, there is a continuing need for new derivatives which are either more active then the currently known fortimicins, or which can be used against bacteria which have become or will become resistant to the known antibiotics. The present invention provides such derivatives.

Fortimicin E is coproduced with Fortimicin A and B by the fermentation of a microorganism belonging to the genus Micromonospora. Structurally, Fortimicin E is the $C_3$, $C_4$ epimer of Fortimicin B and thus can so be named as 3-epi,4-epifortimicin B. The 4-N-acyl derivatives of Fortimicin B are disclosed and claimed in our concurrently filed and co-assigned U.S. Patent application Ser. No. 863,012, filed Dec. 21, 1977.

SUMMARY OF THE DISCLOSURE

4-N-acyl, 2'-N-acyl and 4,2'-N,N'-diacyl Fortimicin E derivatives are provided by the present invention. The new antibiotics are effective against various Gram-negative and Gram-positive bacteria and can be administered orally or parenterally in daily dosages of from about 1 to about 100 mg/kg of body weight daily to mammalian patients showing symptoms of infection caused by one or more susceptible bacteria.

The compounds can also be used as preservatives for various industrial solutions, in antibacterial scrub solutions for cleaning laboratory bench tops and the like.

The 4-N-acyl Fortimicin E derivatives of this invention are amines and form salts with fluosilicic acid which are useful as mothproofing agents according to the teachings of U.S. Pat. Nos. 1,915,334 and 2,075,359. They also form salts with thiocyanic acid which condense with formaldehyde to form resinous materials useful as pickling inhibitors as taught in U.S. Pat. Nos. 2,425,320 and 2,606,155.

Derivatives useful in the preparation of the compounds of this invention are provided as well as method of making and using the compounds and compositions employing the compounds.

DETAILED DESCRIPTION OF PREFERRED EMBODIMENTS

The 4-N-acylfortimicin E derivatives of this invention are represented by Formula I:

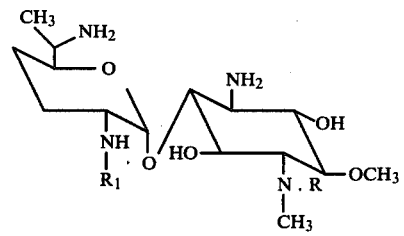

wherein R is hydrogen, acyl, aminoacyl, N-loweralkylaminoacyl, N,N-diloweralkylaminoacyl, hydroxy-substituted aminoacyl or an amino acid residue; $R_1$ is hydrogen, acyl, aminoacyl, N-loweralkylaminoacyl, N,N-diloweralkylaminoacyl, hydroxy-substituted aminoacyl, or an amino acid residue, with the limitation that R cannot be hydrogen when $R_1$ is hydrogen and $R_1$ cannot be hydrogen when R is hydrogen; and the pharmaceutically acceptable salts thereof.

The term "pharmaceutically acceptable salts" refers to non-toxic acid addition salts of the bases which are generally prepared by reacting the base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like salts.

The term "acyl" refers to groups represented by the formula

wherein $R_1$ is loweralkyl, i.e., formyl, acetyl, propionyl, butyryl, etc.

"Lower alkyl" refers to straight or branched chain alkyl radicals having from 1 to 6 carbon atoms, i.e., methyl, ethyl, n-propyl, iso-propyl, n-butyl, sec-butyl, tert-butyl, n-pentyl, 2-methylbutyl, n-hexyl, 2-methylpentyl, 3-methylpentyl, 2,2-dimethylbutyl and the like.

The term "amino acid residue" refers to D, L, or DL amino acid residues and includes but is not limited to glycyl, alanyl, sarcosyl, tyrosyl, phenylalanyl, methionyl, seryl, lysyl, asparaginyl, isoleucyl, leucyl, threonyl, valyl, prolyl, glutaminyl, tryptophanyl, glutamyl and the like.

The present invention also provides intermediates of Fortimicin E represented by Formula II and III:

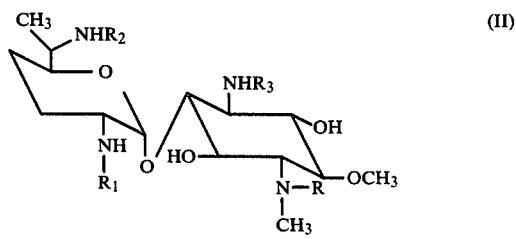

wherein $R_1$, $R_2$ and $R_3$ are each hydrogen or benzyloxycarbonyl and R is as defined in Formula I or RZ wherein Z is benzyloxycarbonyl, with the limitation that R must be RZ when $R_1$, $R_2$ and $R_3$ are hydrogen; and the pharmaceutically acceptable salts thereof.

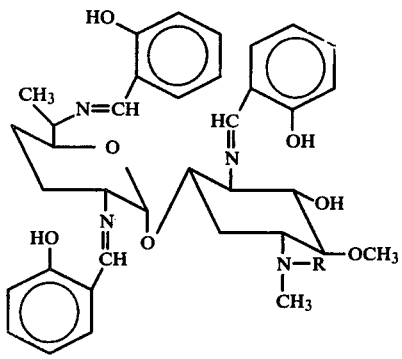
(III)

wherein R is hydrogen, or as defined in Formula I, or RZ wherein Z is benzyloxycarbonyl.

Generally speaking, the 4-N-acyl fortimicin E derivatives of this invention can be prepared by reacting 3 moles of salicyaldehyde with fortimicin E, which results in the formation of 1,2',6'-tri-N-salicylaldehyde Schiff base fortimicin E. The latter can then be aminoacylated by coupling the Schiff base intermediate with an active ester represented by the formula A-R, i.e., N-benzyloxycarbonylglycyl-N-hydroxysuccinimide active ester (A=ONS, R=COCH$_2$—NH—Z), N-benzyloxycarbonyl-β-alanyl N-hydroxy-5-norbornene-2,3-dicarboximide active ester (A=ONB, R=COCH$_2$—NH—Z), N-benzyloxycarbonylsarcosyl N-hydroxy-5-norborene-2,3-dicarboximide active ester (A=ONB, R=COCH$_2$—N(CH$_3$)—Z), and N-benzyloxycarbonyl-L-(2-hydroxy-4-amino)butyryl N-hydroxy-5-norbornene-2,3-dicarboximide active ester (A=ONB, R=COCH(OH)CH$_2$CH$_2$—NH—Z) where the symbol Z refers to the benzyloxycarbonyl group

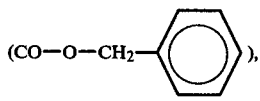

ONB refers to N-benzyloxycarbonyl norbornyl dicarboximide and ONS refers to N-(benzyloxycarbonyl)-succinimide. The following products are obtained after the above, illustrative couplings: 4-N-(N-benzyloxycarbonyl)glycyl-1,2',6'-tri-N-salicylaldehyde Schiff base fortimicin E (R=COCH$_2$—NH—Z), 4-N-(N-benzyloxycarbonyl)β-alanyl-1,2',6'-tri-N-salicylaldehyde Schiff base fortimicin E (R=COCH$_2$CH$_2$—NH—Z), 4-N-(N-benzyloxycarbonyl) sarcosyl-1,2',6'-tri-N-salicylaldehyde Schiff base fortimicin E (R=COCH$_2$—N(CH$_2$)—Z), and 4-N-[N-benzyloxycarbonyl-L-(2-hydroxy-4-amino)butyryl]-1,2',6'-tri-N-salicylaldehyde Schiff base fortimicin E (R—COCH(OH)CH$_2$CH$_2$—NH—Z), respectively.

The Schiff base intermediates are treated with 0.2 N aqueous hydrochloric acid to cleave the Schiff base protecting groups and the resulting crude trihydrochloride salts are subjected to silica gel chromatography in solvent system, containing ammonium hydroxide which results in the following illustrative, partially deprotected intermediates: 4-N-(N-benzyloxycarbonyl)-glycylfortimicin E (R=COCH$_2$—NH—Z); 4-N-(N-benzyloxycarbonyl)β-alanylfortimicin E (R=COCH$_2$CH$_2$—NH—Z); 4-N-(N-benzyloxycarbonyl)sarcosylfortimicin E (R=COCH$_2$-N(CH$_3$)-Z); and 4-N-[N-benzyloxycarbonyl-L-(2-hydroxy-4-amino)butyryl]fortimicin E (R=COCH(OH)CH$_2$CH$_2$-NH-Z), respectively. The 4-N- protected intermediates are then reacted with N-benzyloxycarbonyl-5-norbornene-2,3-dicarboximide (Z-ONB) to form the following tetraprotected compounds: N-benzyloxycarbonyl-4-N-glycylfortimicin E (R=COCH$_2$—NH—Z), N-benzyloxycarbonyl-4-N-β-alanylfortimicin E (R=COCH$_2$CH$_2$—NH—Z), N-benzyloxycarbonyl-4-N-sarcosylfortimicin E (R=COCH$_2$—N(CH$_3$)—Z), and N-benzyloxycarbonyl-L-(2-hydroxy-4-amino)-butyrylfortimicin E (R=COCH(OH)CH$_2$CH$_2$—N-H—Z), respectively.

4-N-acyl derivatives of Formula I can be prepared by hydrogenolysis of the tetra-N-benzyloxycarbonyl intermediates over a palladium on carbon catalyst (5% Pd-C) in 0.2 N hydrochloric acid in methanol. The following illustrative 4-N-acylaminofortimicin E tetrahydrochloride salts are prepared in this manner: 4-N-glycylfortimicin E tetrahydrochloride salt (R=COCH$_2$—NH$_2$), 4-N-β-alanylfortimicin E tetrahydrochloride salt (R=COCH$_2$CH$_2$—NH$_2$), 4-N-sarcosylfortimicin E tetrahydrochloride salt (R=COCH$_2$CH$_2$—NH—CH$_3$), and 4-N-L-(2-hydroxy-4-amino)butyrylfortimicin E tetrahydrochloride salt (R=COCH(OH)CH$_2$CH$_2$—NH$_2$), respectively.

Fortimicin E can be prepared by the fermentation of *Micromonospora olivoasterosprora* ATCC 21819 in a suitable fermentation broth and isolated as described hereinbelow.

The following examples further illustrate the present invention.

Examples 1–4 illustrate the preferred method of producing and isolating fortimicin E from the fermentation broth.

EXAMPLE 1

Preparation of Fermentation Broth

6000 Liters of a fermentation broth having the following composition and pH 7 before sterilization is prepared:

| Ingredient | Weight Percent |
|---|---|
| Starch | 4.00 |
| Soybean meal | 2.00 |
| Cornsteep liquor | 0.05 |
| K$_2$HPO$_4$ | 0.05 |
| MgSO$_4$ . 7H$_2$O | 0.05 |
| KCl | 0.03 |
| CaCO$_3$ | 0.1 |
| Water | to 100.00 |

EXAMPLE 2

Preparation of Inoculum

*Micromonospora olivoasterospora* ATCC 21819 is used as a seed strain and is initially cultured in a first seed medium containing 2% glucose, 0.5% peptone, 0.5% yeast extract and 0.1% calcium carbonate (pH 7.2 before sterilization) by inoculating one loopful of the seed strain into 10 ml of the seed medium in a 50 ml large test tube. Culturing is carried out at 30° C. for 5 days with shaking. Ten ml of the seed culture broth is then inoculated into 30 ml of a second seed medium in a 250 ml Erlenmeyer flask. The composition of the second seed medium is the same as that of the first seed medium. The second seed culturing is carried out at 30° C. for two days with shaking.

Then 30 ml of the second seed culture broth is inoculated into 300 ml of a third seed medium in a 2 l Erlenmeyer flask provided with baffles. The composition of the third seed medium is the same as that of the first seed medium and the third seed culturing is carried out at 30° C. for 2 days with shaking. Thereafter 1.5 l of the third seed culture broth (corresponding to the content of five flasks) is inoculated into 15 l of a fourth seed medium in a 30 l glass jar fermenter. The composition of the fourth seed medium is the same as that of the first seed medium. Culturing in the jar fermenter is carried out at 30° C. for two days with aeration and stirring (revolution: 350 r.m.p., aeration: 15 l/min.).

EXAMPLE 3

Production of Fortimicin E 15 l of the fourth seed culture broth of Example II is inoculated into 150 l of a main fermentation medium in a 300 l stainless steel fermenter. The main fermentation medium comprises: 4% starch, 2% soybean meal, 1% corn steep liquor, 0.05% $K_2HPO_4$, 0.05% $MgSO_4$.$7H_2O$, 0.03% KCl and 0.1% $CaCO_3$ and water (pH 7.0 before sterilization). Culturing in the fermenter is carried out at 30° C. for 4 days with aeration and stirring (revolution: 150 r.p.m.; aeration: 80 l/min.).

EXAMPLE 4

Isolation of Fortimicin E

To 500 liters of the fermentation broth prepared as above described is added 102 liters of a weakly acidic carboxylic (polymethacrylate) type cation exhange resin in the ammonia form, e.g. Amberlite IRC-50 sold by Rohm and Haas Company. The mixture is agitated for two hours, during which time the mixture is maintained at pH 6.6 by the addition of sulfuric acid. The ion exchange resin is separated from the broth by centrifugation and then added to a column and backwashed with deionized water until free of extraneous solids. The columm is washed with water, then eluted downflow with 1 N ammonium hydroxide. Elutes of pH 9.6 to about 11.3 are collected and concentrated under reduced pressure until excess ammonia is removed. The solution is adjusted to pH 2.0 with hydrochloric acid and treated with 5% (w/v) activated carbon such as Pittsburgh RB carbon sold by Calgon Corporation. The solution is then filtered through a diatomaceous earth mat and the filtrant concentrated under reduced pressure to give a mixture of crude fortimicins and metabolites.

A portion of the crude fortimicins (265 grams), prepared as described above, is dissolved in 8 liters of water and the solution adjusted to pH 9.0 with ammonium hydroxide. To facilitate isolation of fortimicin E, fortimicin A is hydrolyzed to fortimicin B by heating the solution to 70° C. for 20 hours, maintaining a pH 9.0 by the controlled addition of ammonium hydroxide. After filtration through a mat of diatomaceous earth, the reaction mixture is concentrated under reduced pressure to approximately 3.6 liters. A portion of this material (1.8 liters) is diluted to 15 liters with water and adjusted to pH 6.8 with hydrochloric acid. The solution is charged on a column containing 7 liters of a weakly acidic, carboxylic (polymethacrylic) type, cation exchange resin in the ammonia form, e.g. Amberlite JRC-50. After washing with water, the column is eluted with 20 liters of 0.1 N ammonium hydroxide. One liter fractions are collected and examined by thin layer chromatography using Whatman No. 1 filter paper. Development is carried out at room temperature for 10 to 15 hours using a solvent system consisting of the lower phase of a mixture of methanol-chloroform-concentrated ammonium hydroxide (1:1:1 v/v).

Fractions 1-2: Unidentified minor components
Fractions 3-4: Isofortimicin
Fraction 5: Isofortimicin and fortimicin B
Fractions 6-10: Fortimicin B
Fractions 11-20: Unidentified minor components Continued elution of the column with 1 N ammonium hydroxide gives fractions containing fortimicin E as the major component.

Lyphilization of the active fraction yields 22 g. of fortimicin E.

An analytical sample of fortimicin E is prepared by further chromatography on a column of silica gel, prepared and eluted with a solvent system consisting of the lower phase of a mixture of methanol-chloroform-concentrated ammonium hydroxide (1:1:1 v/v). Chromatography of 1 g. of crude fortimicin E, prepared as described above, yields 0.632 g. of pure antibiotic as the free base.

The following examples illustrate the present invention.

EXAMPLE 5

1,2',6'-Tri-N-salicylaldehyde Schiff base Fortimicin E

A solution of 1.310 g of fortimicin E and 1.490 g of salicylaldehyde in 30 ml of methanol is refluxed and stirred for 1 hour. The solvent is evaporated under reduced pressure and the residue is dissolved in 30 ml of benzene which is likewise evaporated under reduced pressure. This last process is repeated six times. The residue is dried under high vacuum over KOH pellets to yield: 2.837 g of product; IR($CDCl_3$) 1622, 1575 cm$^{-1}$.

EXAMPLE 6

4-N-(N-benzyloxycarbonyl)glycyl-1,2',6'-tri-N-salicylaldehyde Schiff base Fortimicin E A solution of the above prepared 1,2',6'-tri-N-salicylaldehyde Schiff base fortimicin E, 2.837 g, and 2.054 g of N-benzyloxycarbonylglycyl N-hydroxysuccinimide active ester in 25 ml of tetrahydrofuran is stirred at room temperature overnight. The solvent is evaporated under reduced pressure to afford a residue of 4.861 g of the desired product.

EXAMPLE 7

4-N-(N-benzyloxycarbonyl)glycyl fortimicin E

The substance obtained above (4.861 g) is dissolved in 500 ml of chloroform and the solution is shaken with 500 ml of 0.2 N aqueous hydrochloric acid. The layers are separated and the chloroform solution is extracted with three 150 ml portions of 0.2 N aqueous hydrochloric acid. The hydrochloric acid extracts are washed in series with three 250 ml portions of chloroform. The chloroform solutions are dried over anhydrous sodium sulfate, filtered, combined and evaporated to leave a residue of 1.413 g of nonbasic substances. The latter are not characterized.

The 0.2 N aqueous hydrochloric acid extracts are evaporated under reduced pressure at room temperature. The residue is dissolved in 60 ml of methanol and the solvent is likewise evaporated. This last process is repeated six times. The residue is dried over potassium hydroxide pellets under high vacuum to afford 2.737 g of crude 4-N-(N-benzyloxycarbonyl)glycylfortimicin E trihydrochloride salt.

A partial purification of 2.737 g of the above residue by chromatography on 270 g of silica gel using the lower phase of a mixture of chloroform-methanol-concentrated aqueous ammonium hydroxide (1:1:1 v/v) as the eluting solvent system afforded 1.426 g of a mixture containing the desired 4-N-(N-benzyloxycarbonyl)-glycylfortimicin E. Further chromatography of this residue (1.426 g) on 180 g of silica gel using the lower phase of a chloroform-methanol-concentrated aqueous ammonium hydroxide-water (2:2:1:1 v/v) mixture as the solvent system leads to the separation of several components. Evaporation of the solvent from the early chromatographic fractions leads to the isolation of 0.071 g of nonpolar substances which are not further characterized. A next group of fractions affords, after evaporation of the solvent, 0.108 g of 4,2'-di-N-(N-benzyloxycarbonyl)glycylfortimicin E: IR(KBr pellet) 1710, 1640, 1530 cm$^{-1}$; PMR (D$_2$O) $\delta$7.84 (Z-Ar), 3.28 (subst. N—CH$_3$), 1.56 (d, 7'—CH$_3$) ppm. Later fractions of the chromatogram results in 1.083 g of the desired 4-N-(N-benzyloxycarbonyl)glycylfortimicin E: IR(KBr pellet) 1705, 1635 cm$^{-1}$; PMR (D$_2$O) $\delta$7.85 (Z-Ar), 5.56 (CH$_2$—Z), 3.91, 3.85 (OCH$_3$, two signals are caused because of hindered rotation), 3.35 (subst. N—CH$_3$), 1.45 (d, 7'—CH$_3$) ppm.

EXAMPLE 8

N-Oxybenzyloxycarbonyl-5-norbornene-2,3-dicarboximide

To an ice-cooled suspension of 30.00 g of N-hydroxy-5-norbornene-2,3-dicarboximide in 150 ml of water are added 7.06 g of sodium hydroxide pellets over a period of 10 minutes with stirring. Methanol is added to the ice-bath to bring the temperature to $-5°$ C. and the contents of the flask are stirred for 10 minutes. Twenty-three ml of benzyloxycarbonyl chloride are then added to the stirred solution over a period of 15 minutes. The mixture is then stirred at $-5°$ C. for 2 hours and then at room temperature for 24 hours. The reaction mixture is extracted with 400 ml of chlorofrom, and the chloroform extract washed with three 200 ml portions of water. The aqueous washes are then extracted in series with four 200 ml portions of chloroform. The chloroform extracts are dried over anhydrous magnesium sulfate, filtered, combined and evaporated to leave a residue of 39.88 g. The crude material is recrystallized from 95% ethanol. The crystals which form upon cooling are collected on a filter and washed with several small portions of cold ethanol. After drying, 29.11 g of product as crystal are obtained, mp. 126°-127°. A sample is recrystallized twice more for analysis: m.p. 126°-127°; IR(CDCl$_3$) 1800 (shoulder), 1782, 1732 cm$^{-1}$; PMR (CDCl$_3$) $\delta$7.41 (Z-Ar), 6.2 (vinyl H), 5.31 (CH$_2$—Z), 3.4 (H single proton), 1.7 (CH$_2$) ppm.

Anal. Calcd. for C$_{17}$H$_{15}$NO$_5$: C, 65.17; H, 4.83; N, 4.47%. Found: C, 65.02; H, 4.82; N, 4.26%.

EXAMPLE 9

Tetra-N-benzyloxycarbonyl-4-N-glycylfortimicin E

A solution containing 1.030 g of the above prepared 4-N-(N-benzyloxycarbonyl)glycylfortimicin E (Example 7) and 2.025 g of N-oxybenzyloxycarbonyl-5 -norbornene-2,3-dicarboximide (Example 8 ) in 56 ml of methanol are stirred at room temperature overnight. Evaporation of the solvent under reduced pressure leaves a residue of 3.056 g of crude reaction mixture. The latter is purified by repeated silica gel column chromatography using benzene-methanol-ethanol (1170:34:136 v/v) and benzene-chloroform-ethyl acetate-n-propanol (13:16:8:3 v/v) as the eluting systems.

From a first group of fractions preceding the larger amount of substance, 0.078 g of an unidentified new compound was isolated after evaporation of the solvent. This material is chromatographed once more on silica gel using ethyl acetate-ethanol (98:2 v/v) as the eluent to give an analytically pure compound: $[\alpha]_D^{25}+49°$ (c, 1.00 in CHCl$_3$), IR (CDCl$_3$) 1698, 1640, 1502 cm$^{-1}$; PMR (CDCl$_3$) $\delta$7.28 (Z—Ar), 5.01 (CH$_2$—Z), 3.48 (OCH$_3$), 2.95 (substituted N—CH$_3$), 0.89 (C$_{7'}$—CH$_3$) ppm.

Anal. Calcd. for C$_{49}$H$_{59}$N$_5$O$_{14}$: C, 62.47; H, 6.31; N, 7.44%. Found: C, 62.19; H, 6.54; N, 7.40%.

This compound clearly carries a 4-N-glycyl group and has the atomic composition of the desired product (see below) or of tetra-N-benzyloxycarbonylfortimicin A. However, it is not identical to either of these substances and therefore represents a new compound.

Combination of the appropriate fractions following the minor component in the original chromatograms and evaporation of the solvents left a residue of 1.415 g of the desired tetra-N-benzyloxycarbonyl-4-N-glycylfortimicin E.

An analytical sample was obtained after re-chromatography of a part of the above product on silica gel using benzene-methanol-ethanol (1170:36:136 v/v) as the element: $[\alpha]_D^{24}+32°$ (c, 0.99 in CHCl$_3$); IR (CDCl$_3$) 1690, 1642, 1500 cm$^{-1}$; NMR (CDCl$_3$) $\delta$7.28 (Ar—Z), 5.02 (CH$_2$—Z), 3.43 (OCH$_3$); 2.82 (substituted N-CH$_3$), 0.92 (C$_{7'}$—CH$_3$) ppm.

Anal. Calcd. for C$_{49}$H$_{59}$N$_5$O$_{14}$: C, 62.47; H, 6.31; N, 7.44%. Found: C, 62.64; H, 6.43; N, 7.41%.

EXAMPLE 10

4-N-glycylfortimicin E tetrahydrochloride salt

A solution of 0.400 g of tetra-N-benzyloxycarbonyl-4-N-glycylfortimicin E (Example 9) in 34 ml of 0.2 N hydrochloric acid in methanol and 16 ml of methanol was hydrogenolyzed over 5% Pd C for 4 hours. The catalyst is collected on a filter and washed with methanol. The filtrate is evaporated under reduced pressure, the residue is redissolved in methanol and this solvent evaporated. This last procedure is repeated six times to yield 0.235 g of the desired product after drying in vacuo over potassium hydroxide pellets: $[\alpha]_D^{25}+54°$ (c, 1.00 in CH$_3$OH); IR (KBr-pellet) 1640, 1485 cm$^{-1}$; PMR (DMSO, 150°) $\delta$6.25 (anomeric H), 3.46 (OCH$_3$), 2.94 (substituted N-CH$_3$), 1.31 (C$_{7'}$—CH$_3$) ppm; M+ calcd. for C$_{17}$H$_{35}$N$_5$O$_6$: 405.2587, found 405.2605; the NMR spectra is consistent with the structure product.

EXAMPLE 11

4-N-(N-benzyloxycarbonyl)-β-alanylfortimicin E

A solution of 2.579 g of 1,2',6'-tri-N-salicylaldehyde Schiff base, prepared from 1.205 g of fortimicin E according to the procedure of Example 5, and of 2.500 g of the N-benzyloxycarbonyl-β-alanyl active ester of N-hydroxy-5-norbornene-2,3-dicarboximide, prepared by the method of M. Fujino et al., *Chem. Pharm. Bull. Japan*, 22, 1857 (1974), in 30 ml of tetrahydrofuran is stirred at room temperature for 25 hours. Evaporation of the solvent under reduced pressure yields 5.079 g of crude product.

This material is dissolved in 500 ml of chloroform and the solution is shaken with 500 ml of 0.2 N hydrochloric acid. The layers are separated and the chloroform solution is extracted with three 150 ml portions of 0.2 N hydrochloric acid. The acid extracts are washed in series with three 25 ml portions of chloroform. The chloroform washes are dried over anhydrous magnesium sulfate, filtered, combined, and evaporated to yield 2.221 g of non-basic material. The acidic extracts are combined and evaporated under reduced pressure at low temperature. The residue is dissolved in 30 ml of methanol which is likewise evaporated. This last process is repeated six times to yield a residue of 2.630 g of reaction products as the hydrochloride salts after drying is vacuo over potassium hydroxide. The above hydrochloride salts (2.630 g) are chromatographed on 170 g of silica gel using the lower layer of a chloroform-methanol-concentrated ammonium hydroxide (1:1:1 v/v) mixture as the eluting solvent. Combination of the fractions containing the desired 4-N-(N-benzyloxycarbonyl)β-alanylfortimicin E and evaporation of the solvents affords 0.806 g of residue. This substance is re-chromatographed on 170 g of silica gel using the lower phase of a chloroform-methanol-concentrated ammonium hydroxide-water (2:2:1:1 v/v) mixture as the eluting solvent. After combination and evaporation of the solvents from the appropriate fractions, 0.794 g of the desired product is obtained: IR(KBr-pellet) 1695, 1613 cm$^{-1}$; PMR (D$_2$O) δ7.82 (Ar—Z), 5.5 (CH$_2$—Z), 3.85 (O—CH$_3$), 3.32 (substituted N—CH$_3$), 1.49 (C$_{7'}$—CH$_3$) ppm.

EXAMPLE 12

Tetra-N-benzyloxycarbonyl-4-N-β-alanylfortimicin E

A solution of 0.754 g of the above prepared 4-N-(N-benzyloxycarbonyl)β-alanylfortimicin E and 1.440 g of N-oxybenzyloxycarbonyl-5-norbornene-2,3-dicarboximide in 40 ml of methanol is stirred at room temperature for 24 hours. Evaporation of the solvent leaves a residue of 2.179 g which is chromatographed on 180 g of silica gel using a methylene chloride-methanol-concentrated ammonium hydroxide (185:15:2 v/v) mixture as the eluent. Combination of the fractions containing the desired substance and evaporation of the solvent yields 0.539 g of partially purified product. Repeated chromatography of this sample on silica gel using benzene-methanol-ethanol (1170:34:136 v/v), methylene chloride-methanol-concentrated ammonium hydroxide (185:15:2 v/v) yields 0.415 g of pure tetra-N-benzyloxycarbonyl-4-N-β-alanylfortimicin E: $[\alpha]_D^{24}$+29° (c, 1.02 in CHCl$_3$); IR(CDCl$_3$) 1697, 1627, 1502 cm$^{-1}$; PMR (CDCl$_3$) δ7.28 (Ar—Z), 5.02 (CH$_2$—Z), 3.4 and 3.37 (OCH$_3$), 2.82 and 2.75 (substituted N—CH$_3$), 0.9 (C$_{7'}$—CH$_3$) ppm. The two signals observed for OCH$_3$ and N—CH$_3$ are due to hindered rotation.

Anal. Calcd. for C$_{50}$H$_{61}$N$_5$O$_{14}$: C, 62.81; H, 6.43; N, 7.33%. Found: C, 62.67; H, 6.58; N, 7.28%.

EXAMPLE 13

4-N-β-lanylfortimicin E tetrahydrochloride salt

A solution of 0.363 g of tetrabenzyloxycarbonyl-4-N-β-alanylfortimicin E in 30 ml of 0.2 N hydrochloric acid in methanol and 20 ml of methanol is hydrogenolyzed over 0.360 g of 5% Pd C for 4 hours. The catalyst is collected on a filter and washed with several small portions of methanol. The filtrate is evaporated under reduced pressure and the residue is dissolved in 30 ml of methanol which is likewise evaporated under reduced pressure. This last process is repeated six times to afford a residue of 0.213 g of product after drying in vacuo over potassium hydroxide pellets: $[\alpha]_D^{26}$+48° (c, 1.04 in CH$_3$OH); IR(KBr-pellet) 1618, 1482 cm$^{-1}$; PMR (DMSO, 150°) δ3.43 (O—CH$_3$), 2.88 (substituted N—CH$_3$), 1.3 (C$_{7'}$—CH$_3$) ppm; M$^+$ calcd. for C$_{18}$H$_{37}$O$_6$: 419.2744, found M$^+$ m/e 419.2747.

EXAMPLE 14

N-Benzyloxycarbonylsarcosyl active ester of N-hydroxy-5-norbornene-2,3-dicarboximide To a solution of 4.471 g of N-benzyloxycarbonylsarcosine and 3.754 g of N-hydroxy-5-norbornene-2,3-dicarboximide in 15 ml of tetrahydrofuran and 15 ml of dioxane there is added 4.235 g of N,N-dicyclohexylcarbodiimide in 2 ml of tetrahydrofuran and 2 ml of dioxane according to the process of M. Fujino et al. *Chem. Pharm. Bull., Japan*, 22, 1857 (1974). The mixture was stirred at room temperature overnight. The dicyclohexylurea which had precipitated from the reaction mixture is collected on a filter and washed with a total of 20 ml of tetrahydrofuran dioxane (1:1 v/v). Evaporation of the solvent from the filtrate affords 8.523 g of crude product. The substance is recrystallized from isopropanol to yield 4.294 g of the active ester, mp 75°-80°. Concentration of the mother liquors yields an additional 4.125 g of less pure product, m.p. 69°-73°.

A portion of the first crop is recrystallized for analysis: mp 80°-82°; IR(CDCl$_3$) 1821, 1774, 1725, 1700 (shoulder) cm$^{-1}$; NMR (CDCl$_3$) δ7.32 (Ar—Z), 6.17 (vinyl), 5.13 (CH$_2$—Z), 4.3 (sar-CH$_2$), 3.35 (single H), 3.0 (sar-CH$_3$), 1.64 (—CH$_2$) ppm.

Anal. Calcd. for C$_{20}$H$_{20}$N$_2$O$_6$: C, 62.49; H, 5.24; N, 7.29%.

Found: C, 62.65; H, 5.28; N, 7.24%.

EXAMPLE 15

4-N-(N-benzyloxycarbonyl)sarcosylfortimicin E

A solution of 2.433 g of 1,2',6'-tri-N-salicylaldehyde Schiff base fortimicin E prepared from 1.202 g of fortimicin E according to the procedure outlined in Example 5, and 2.500 g of the N-benzyloxycarbonylsarcosyl active ester of N-hydroxy-5-norbornene-2,3-dicarboximide of Example 14 in 25 ml of tetrahydrofuran was stirred for 24 hours at room temperature. Evaporation of the solvent under reduced pressure affords a residue of 5.025 g of crude product.

This material is dissolved in 500 ml of chloroform and the solution is shaken with 500 ml of 0.2 N aqueous hydrochloric acid. The layers are separated and the chloroform solution is extracted with three 150 ml portions of 0.2 N hydrochloric acid. The acid extracts are washed in series with three 250-ml portions of chloroform. The chloroform washes are dried over anhydrous sodium sulfate, filtered, combined and evaporated to leave 2.690 g of non-basic material.

The acidic extracts are combined and evaporated under reduced pressure at low temperature. The residue is taken up in 30 ml of methanol which is likewise evaporated (6×), yielding 2.151 g of reaction products after drying in vacuo over potassium hydroxide pellets.

The above hydrochloride salts (2.515 g) are chromatographed on 160 g of silica gel using the lower phase of a chloroform-methanol-concentrated ammonium hydroxide (1:1:1 v/v) mixture as the eluting solvent. The fractions containing the desired 4-N-(N-benzyloxycarbonyl)sarcosylfortimicin E are combined and the solvents evaporated yielding 0.651 g of crude product which is rechromatographed on 160 g of silica gel using the lower phase of a chloroform-methanol-concentrated ammonium hydroxide-water (2:2:1:1 v/v) mixture as the eluting solvent. After combination of the appropriate fractions and evaporation of the solvents, 0.155 g of 4-N-(N-benzyloxycarbonyl)sarcosylfortimicin E is obtained: IR(KBr-pellet) 1693, 1644 cm$^{-1}$; PMR (D$_2$O) $\delta$7.85 (Z—Ar), 5.56 (CH$_2$—Z), 3.38 and 3.35 (subst. N—CH$_3$) and Sar-N-CH$_3$), 1.47 (C$_{7'}$—CH$_3$) ppm.

EXAMPLE 16

Tetra-N-benzyloxycarbonyl-4-N-sarcosylfortimicin E

A solution of 0.155 g of 4-N-(N-benzyloxycarbonyl)-sarcosylfortimicin E and 0.297 g of N-oxybenzyloxycarbonyl-5-norbornene-2,3-dicarboximide in 10 ml of methanol is stirred at room temperature overnight. Evaporation of the solvent under reduced pressure affords 0.444 g of residue which is chromatographed on 70 g of silica gel using a benzene-methanol-ethanol (1170:34:136 v/v) mixture as the eluent. Combination of the appropriate fractions and evaporation of the solvent yields 0.228 g of partially purified tetra-N-benzyloxycarbonyl-4-N-sarcosylfortimicin E. A second chromatogram of this substance on 50 g of silica gel, employing the same solvent system, yields 0.166 g of the desired product in pure form: $[\alpha]_D^{24}$+30° (c, 0.96 in CHCl$_3$); IR (CDCl$_3$) 1690, 1655 (shoulder), 1500 cm$^{-1}$; PMR (CDCl$_3$) $\delta$7.3 (Ar—Z), 5.02 (CH$_2$—Z), 3.48 (OCH$_3$), 2.94 and 2.8 (Sar—N—CH$_3$), 4-N—CH$_3$), 0.93 (C$_{7'}$—CH$_3$) ppm.

Anal. Calcd. for C$_{50}$H$_{61}$N$_5$O$_{14}$: C, 62.81; H, 6.43; N, 7.33%. Found: C, 62.52; H, 6.41; N, 7.25%.

EXAMPLE 17

4-N-sarcosylfortimicin E tetrahydrochloride salt

A solution of 0.145 g of tetra-N-benzyloxycarbonyl-4-N-sarcosylfortimicin E in 12 ml of 0.2 N hydrochloric acid in methanol and 23 ml of methanol is hydrogenolyzed over 0.150 g of a 5% Pd/C catalyst for 4 hours. The catalyst is collected on a filter and washed with methanol. The filtrate is evaporated to dryness under reduced pressure and the residue is dissolved in 20 ml of methanol which is likewise evaporated. The last procedure is repeated six times. The residue is dried in vacuo over potassium hydroxide pellets to afford 0.082 g of product: $[\alpha]_D^{22}$+52° (c, 1.06 in CH$_3$OH); IR (KBr-pellet) 1640 cm$^{-1}$; PMR (DMSO) $\delta$6.29 (anomeric-H), 3.43 (O—CH$_3$), 2.78 and 2.56 (C$_4$—4-N—CH$_3$ and Sar—N—CH$_3$), 1.26 (C$_{7'}$—CH$_3$) ppm.; M$^+$ calcd. for C$_{18}$H$_{37}$N$_5$O$_6$: 419.2744, found: 419.2738.

EXAMPLE 18

4-N-[N-benzyloxycarbonyl-L-(2-hydroxy-4-amino)-butyryl]fortimicin E

The N-hydroxy-5-norbornene-2,3-dicarboximide active ester of L-N-benzyloxycarbonyl-2-hydroxy-4-aminobutyric acid is prepared according to M. Fujino et al. *Chem. Pharm. Bull. Japan,* 22, 1857 (1974). To an ice cold solution of 1.645 g of L-N-benzyloxycarbonyl-2-hydroxy-4-aminobutyric acid and 1.182 g of N-hydroxy-5-norbornene-2,3-dicarboximide in 16 ml of tetrahydrofuran-dioxane (1:1 v/v), are added, with stirring 1.347 g of N,N'-dicyclohexylcarbodiimide and 5 ml of tetrahydrofuran-dioxane (1:1 v/v). The mixture is stirred at 0° C. for 50 minutes and then at room temperature for 3 hours.

The N,N'-dicyclohexylurea produced by the above reaction is collected on a filter and washed with 10 ml of tetrahydrofuran-dioxane (1:1 v/v). The filtrate is collected in a flask containing 2.649 g of 1,2',6'-tri-N-salicylaldehyde Schiff base fortimicin E, prepared from 1.209 g of fortimicin E according to the method of Example 5. The reaction mixture is stirred at room temperature for 20 hours. Evaporation of the solvent leaves 5.609 g of crude product.

The above substance (5.609 g) is dissolved in 500 ml of chloroform and the solution is shaken with 500 ml of 0.2 N hydrochloric acid. The chloroform phase is separated and extracted with three 150-ml portions of 0.2 N hydrochloric acid. The aqueous phases are washed in series with three 250-ml portions of chloroform. The chloroform solutions are dried over anhydrous sodium sulfate, filtered, combined, and evaporated to afford a residue of 1.884 g of non-basic substances.

The aqueous extracts are combined and evaporated in vacuo at low temperature. The residue is dissolved in 30 ml of methanol and the solvent evaporated. This last process is repeated six times and the resulting material is dried over potassium hydroxide pellets under high vacuum to yield 3.436 g of crude product.

The crude product (3.436 g) is chromatographed on 270 g of silica gel using the lower phase of a chloroform-methanol-concentrated ammonium hydroxide (1:1:1 v/v) mixture as the eluent. The fractions containing the desired substance are combined and evaporation of the solvent yields a residue of 1.302 g of partially purified product.

The above obtained substance is rechromatographed on 180 g of silica gel using the lower phase of a chloroform. methanol-concentrated ammonium hydroxide-water (2:2:1:1 v/v) as the eluent. Combination and evaporation of the fractions containing the desired 4-N-[N-benzyloxycarbonyl-L-(2-hydroxy-4-amino)butyryl]-fortimicin E afforded a residue of 0.885 g of somewhat impure material: IR (KBr-pellet) 1698, 1630, 1523 cm$^{-1}$.

EXAMPLE 19

Tetrahydro-N-benzyloxycarbonyl-4-N-L-(2-hydroxy-4-amino)butyrylfortimicin E

A solution of 0.836 g of the substance prepared above and 1.500 g of N-oxybenzyloxycarbonyl-5-norbornene-2,3-dicarboximide in 40 ml of methanol is stirred at room temperature overnight. Evaporation of the solvent from the reaction mixture under reduced pressure affords a residue of 2.345 g of crude product which is chromatographed on 180 g of silica gel using a mixture of methylene chloride-methanol-concentrated ammonium hydroxide (185:15:2 v/v) as the eluent.

The early fractions of the chromatogram contained 0.938 g of the desired substance contaminated with less polar components. From the subsequent fractions, 0.192 g of tetra-N-benzyloxycarbonyl-4-N-L-(2-hydroxy-4-amino)butyrylfortimicin E is isolated after evaporation of the solvent. Repeated silica gel chromatography of the residue of the early fractions (0.938 g) above using benzene-methanol-ethanol-acetic acid (1170:35:135:10 v/v) and ethyl acetate-ethanol (98:2 v/v) mixtures affords an additional 0.114 g of product. After two more chromatograms on silica gel using ethyl acetate-ethanol (98:2 v/v) as the eluent, 0.224 g of pure tetra-N-benzyloxycarbonyl-4-N-L-(2-hydroxy-4-amino)butyrylfortimicin E.

An analytical sample had the following physical constants: $[\alpha]_D^{25} + 25°$ (c, 0.99 in CHCl$_3$); IR (CDCl$_3$) 1692, 1624, 1497 cm$^{-1}$; PMR (CDCl$_3$, 55°) $\delta$7.28 (Ar—Z), 5.05 (CH$_2$—Z), 3.45 (OCH$_3$), 2.81 (substituted N—CH$_3$), 0.92 (7'—CH$_3$) ppm.

Anal. Calcd. for C$_{51}$H$_{63}$N$_5$O$_{15}$: C, 62.12; H, 6.44; N, 7.10%. Found: C, 61.92; H, 6.53; N, 6.90%.

EXAMPLE 20

4-N-L-(2-hydroxy-4-amino)butyrylfortimicin E tetrahydrochloride salt

A solution of 0.201 g of tetra-N-benzyloxycarbonyl-4-N-L-(2-hydroxy-4-amino)butyrylfortimicin E in 16.3 ml of 0.2 N hydrochloric acid and 8.7 ml of methanol was hydrogenolyzed over 0.200 g of 5% Pd/C for 4 hours. The catalyst is collected on a filter and washed with methanol. The filtrate is evaporated under reduced pressure and the residue is dissolved in 10 ml of methanol which is likewise evaporated. This last process was repeated six times and resulting material is dried under high vacuum over potassium hydroxide pellets to afford 0.125 g of the desired material: $[\alpha]_D^{22} + 46°$ (c, 1.06 in CH$_3$OH); IR (KBr pellet) 1618, 1482 cm$^{-1}$; PMR (DMSO, 140°) $\delta$6.17 (anomeric H), 3.39 (OCH$_3$), several signals in substituted 4-N—CH$_3$ area, not specifically assigned, 1.25 (7'—CH$_3$) ppm. The NMR spectra supported the assigned structure 6d.

EXAMPLE 21

Tetra-N-benzyloxycarbonyl-4,2'-N,N'-diglycylfortimicin E

A solution of the substance (0.108 g) contained in the chromatographic fractions proceeding the 4-N-(N-benzyloxycarbonyl) glycylfortimicin E of Example 7 and 0.128 g of N-oxybenzyloxycarbonyl-5-norbornene-2,3-dicarboximide in 3 ml of methanol is stirred at room temperature overnight. Evaporation of the solvent afforded a residue of 0.225 g which is chromatographed in silica gel using benzene-ethanol-isopropanol (9:1:1 v/v/v) as the eluting solvent. Combination of the appropriate fraction and evaporation of the solvent left a residue of 0.113 g.

A sample for analysis is obtained after rechromatography on silica gel using ethyl acetate-methanol (98:2 v/v) as the eluting solvent: $[\alpha]_D^{23} + 25°$ (c, 1.00 in CDCl$_3$) 1698, 1640, 1502 cm$^{-1}$; PMR (CDCl$_3$) $\delta$7.3 (Ar—Z), 5.02 (CH$_2$—Z, anomeric$^H$), 3.41 and 3.36 (OCH$_3$, hindered rotation), 2.76 (substituted N—CH$_3$), 0.9 (7'—CH$_3$) ppm.

Analysis Called for C$_{51}$H$_{62}$N$_6$O$_{15}$: C, 61.31; H, 6.26; N, 8.41. Found: C, 60.93; H, 6.27; N, 8.81.

EXAMPLE 22

4,2'N,N'-Diglycylfortimicin E Tetrahydrochloride Salt

A solution of 0.075 g of the above-prepared tetra-N-benzyloxycarbonyl-4,2'-N,N'-diglycylfortimicin E in 6 ml of 0.2 N hydrochloric acid in methanol is hydrogenolyzed over 0.080 g. of 5% Pd C for four hours. The catalyst is collected on a filter and washed with several portions of methanol. The filtrate is evaporated under reduced pressure, and the residue redissolved in 15 ml of methanol which was likewise evaporated. This last procedure is repeated six times. The compound is dried over potassium hydroxide pellets under high vacuum to afford 0.051 g. of the desired product: $[\alpha]_D^{21} + 54°$ (c, 0.98 in CH$_3$OH); IR(KBr pellet) 1656, 1492 cm$^{-1}$; PMR(DMSO) $\delta$2.84 (N—CH$_3$), 1.2 (7'—CH$_3$) ppm. The structure is additionally confirmed by its $^{13}$CMR-spectra.

EXAMPLE 23

In Vitro Antibiotic Activity of 4-N-Acyl Fortimicin E Derivatives

The in vitro antibiotic activity is determined by a 2-fold agar dilution method using 10 ml. per petri plate of Mueller-Hinton agar. The agar is inoculated with one loopful (0.001 ml. loop) of a 1:10 dilution of a 24 hour broth culture of the indicated test organism and incubated at 37° C. for 24 hours. The activity of representative derivative is listed in the following Tables. Minimum inhibitory concentrations (MIC) are expressed as mcg/ml.

TABLE I

In Vitro Activity of 4-N-glycylfortimicin E, Tetrahydrochloride

| Microorganism tested | MIC (mcg/ml) |
|---|---|
| Strep. faecalis 10541 | >100. |
| E. coli R$_3$ | >100. |
| Pseudo aeruginosa | >100. |
| Staph aureus Smith | 6.25 |
| E. coli Juhl | 6.25 |
| Bacillus subtilus U. Ill. 10707 | 12.50 |
| Proteus vulgaris JJ | >100. |
| Shigella sonnei 9290 | 25. |
| Sal. typhimurium Ed #9 | 25. |
| Kleb. pneumoniae KY 4262 | 25. |

TABLE II

In Vitro Activity of 4-N-Sarcosylfortimicin E Tetrahydrochloride

| Microorganism tested | MIC (mcg/ml) |
|---|---|
| Strep. faecalis 10541 | >100. |
| E. coli R$_3$ | >100. |
| Pseudo aeruginosa | >100. |
| Staph. aureus Smith | 25. |
| E. coli Juhl | 50. |
| Bacillus subtilus U. Ill. 10707 | 6.25 |
| Proteus vulgaris JJ | >100. |
| Shigella sonnei 9290 | 100. |
| Sal. typhirmurium Ed #9 | 50. |
| Kleb. pneumoniae KY 4262 | 100. |

TABLE III

In Vitro Activity of 4-N-$\beta$-Alanylfortimicin E Tetrahydrochloride

| Microorganism tested | MIC (mcg/ml) |
|---|---|
| Strep faecalis 10541 | >100. |

TABLE III-continued
In Vitro Activity of 4-N-β-Alanylfortimicin E Tetrahydrochloride

| Microorganism tested | MIC (mcg/ml) |
|---|---|
| E. coli R3 | >100. |
| Pseudo aeruginosa | >100. |
| Staph. aureus Smith | 12.5 |
| E. coli Juhl | 25. |
| Bacillus subtilus U. Ill. 10707 | 12.5 |
| Proteus vulgaris JJ | >100. |
| Shigella sonnei 9290 | >100. |
| Sal. typhirmurium Ed #9 | 25. |
| Kleb. pnemoniae KY4262 | 25. |

TABLE IV
In Vitro Activity of 4-N-L-(2-Hydroxy-4-Amino) Butylfortimicin E Tetrachloride

| Microorganism tested | MIC (mcg/ml) |
|---|---|
| Strep. faecalis 10541 | >100. |
| E. coli R3 | >100. |
| Pseudo aeruginosa | >100. |
| Staph. aureus Smith | 25. |
| E. coli Juhl | 50. |
| Bacillus subtilus U. Ill. 10707 | 12.5 |
| Proteus vulgaris JJ | >100. |
| Shigella sonnei 9290 | >100. |
| Sal. typhirmurium Ed #9 | 100. |
| Kleb. pnemoniae KY 4262 | 50. |

The compounds of this invention are active as systemic antibiotics when injected by parenteral routes of administration, i.e., by the intramuscular, intravenous, intraperitoneal or subcutaneous routes of administration. The compounds can also be administered orally in those instances where it is desirable to sterilize the intestinal tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized, by for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 1 to 100 mg/kg of body weight daily are administered to a mammalian patient suffering from an infection caused by susceptable organism.

We claim:

1. A Fortimicin E derivative of the formula

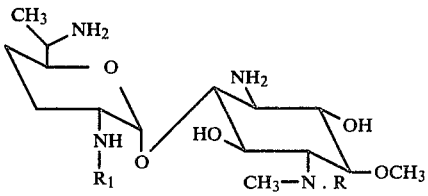

wherein R is hydrogen, acyl, aminoacyl, N-loweralkylaminoacyl, N,N-diloweralkylaminoacyl, hydroxy-substituted aminoacyl or an amino acid residue; and $R_1$ is hydrogen, acyl, amino acyl, N-loweralkylaminoacyl, N,N-diloweralkylaminoacyl hydroxy-substituted aminoacyl or an amino acid residue with the limitation that R cannot be hydrogen when $R_1$ is hydrogen and $R_1$ cannot be hydrogen when R is hydrogen; and the pharmaceutically acceptable salts thereof.

2. A compound of claim 1 wherein R is an amino acid residue and $R_1$ is hydrogen.

3. 4-N-Glycylfortimicin E or a pharmaceutically acceptable salt thereof.

4. 4-N-β-Alanylfortimicin E or a pharmaceutically acceptable salt thereof.

5. 4-N-Sarcosylfortimicin E or a pharmaceutically acceptable salt thereof.

6. A compound of claim 1 wherein R is acyl and $R_1$ is hydrogen.

7. 4-N-acetylfortimicin E or a pharmaceutically acceptable salt thereof.

8. A compound of claim 1 wherein R is hydroxy-substituted aminoacyl and $R_1$ is hydrogen.

9. A compound of claim 1, 4-N-L-(2-hydroxy-4-amino)butyrylfortimicin E or a pharmaceutically acceptable salt thereof.

10. A compound of claim 1 wherein R is hydrogen and $R_1$ is an amino acid residue.

11. A compound of claim 10, 2'-N-glycylfortimicin E, or a pharmaceutically acceptable salt thereof.

12. A compound of claim 10, 2'-N-β-alanylfortimicin E or a pharmaceutically acceptable salt thereof.

13. A compound of claim 10, 2'-N-sarcosylfortimicin E or a pharmaceutically acceptable salt thereof.

14. A compound of claim 1 wherein R and $R_1$ each are an amino acid residue.

15. A compound of claim 14, 4,2'-N,N'-diglycylfortimicin B or a pharmaceutically acceptable salt thereof.

16. A fortimicin E intermediate of the Formula:

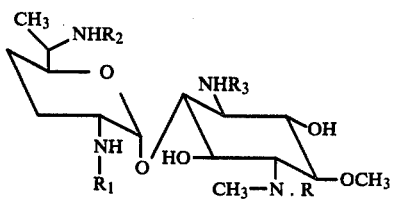

wherein $R_1$, $R_2$ and $R_3$ each are hydrogen or benzyloxycarbonyl and R is acyl, aminoacyl, N-loweralkylaminoacyl, N,N-diloweralkylaminoacyl, hydroxy-substituted aminoacyl, an amino acid residue or RZ, Z being benzyloxycarbonyl; and the pharmaceutically acceptable salts thereof.

17. A fortimicin E intermediate of the Formula:

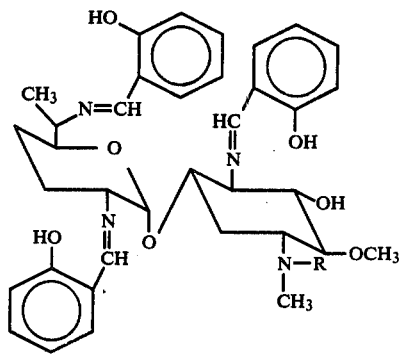

wherein R is hydrogen, acyl, aminoacyl, N-loweralkylamino acyl, N,N-diloweralkylaminoacyl, hydroxy-substituted aminoacyl, an aminoacid residue or RZ, Z being benzyloxycarbonyl; and the pharmaceutically acceptable salts thereof.

18. A pharmaceutical composition comprising a therapeutically effective amount of a compound of claim 1, or a pharmaceutically acceptable carrier or diluent.

* * * * *